US006800060B2

(12) United States Patent
Marshall

(10) Patent No.: US 6,800,060 B2
(45) Date of Patent: Oct. 5, 2004

(54) SWALLOWABLE DATA RECORDER CAPSULE MEDICAL DEVICE

(75) Inventor: Daniel R. Marshall, Boise, ID (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 10/663,939

(22) Filed: Sep. 16, 2003

(65) Prior Publication Data

US 2004/0059204 A1 Mar. 25, 2004

Related U.S. Application Data

(62) Division of application No. 09/710,161, filed on Nov. 8, 2000, now Pat. No. 6,632,175.

(51) Int. Cl.[7] ................................................. A61B 5/00

(52) U.S. Cl. ........................ 600/309; 600/310; 600/343

(58) Field of Search .............................. 600/309, 300, 600/310, 312, 321, 341, 342, 343, 473, 476; 356/39–46; 435/4; 664/891.1, 890.1

(56) References Cited

U.S. PATENT DOCUMENTS

| 427,243 A | 5/1890 | Serrell et al. |
|---|---|---|
| 3,971,362 A | 7/1976 | Pope et al. |
| 4,146,029 A | 3/1979 | Ellinwood, Jr. |
| 4,278,077 A | 7/1981 | Mizumoto |
| 4,425,117 A | 1/1984 | Hugemann et al. |
| 4,439,197 A | 3/1984 | Honda et al. |
| 4,507,115 A | 3/1985 | Kambara et al. |
| 4,585,652 A | 4/1986 | Miller et al. |
| 4,793,825 A | 12/1988 | Benjamin et al. |
| 4,844,076 A | 7/1989 | Lesho et al. |
| 5,170,801 A | 12/1992 | Casper et al. |
| 5,217,449 A | 6/1993 | Yuda et al. |
| 5,279,607 A | 1/1994 | Schentag et al. |
| 5,415,181 A | 5/1995 | Hogrefe et al. |
| 5,557,596 A | 9/1996 | Gibson et al. |
| 5,604,531 A | 2/1997 | Iddan et al. |
| 5,681,260 A | 10/1997 | Ueda et al. |
| 5,792,048 A | 8/1998 | Schaefer |
| 5,797,898 A | 8/1998 | Santini, Jr. et al. |

(List continued on next page.)

FOREIGN PATENT DOCUMENTS

| EP | 0734017 A1 | 9/1996 |
|---|---|---|
| JP | 5007573 A | 1/1993 |

OTHER PUBLICATIONS

"Silicon Micromechanics: Sensors and Actuators On A Chip," Roger T. Howe, Richard S. Muller, Kaigham J. Gabriel and William S. N. Trimmer, pp. 29–35, IEEE Spectrum, Jul. 1990.
"'Camera in a Pill' Views Digestive Tract," The New York Times, Science Desk, May 30, 2000.
"Physical Properties of Thin–Film Field Emission Cathodes With Molybdenum Cones," C. A. Spindt, I. Brodie, L. Humphrey, and E. R. Westerberg, pp. 5248–5263, Journal of Applied Physics, Dec. 1976, vol. 47, No. 12.
"Silicon Field Emission Transistors and Diodes," Gary W. Jones, C. T. Sune, and Henry F. Gray, IEEE Transactions on Components, Hybrids, and Manufacturing Technology, 1051–1055, Dec. 1992, vol. 15, No. 6.
"Bectron Beam–Induced Information Storage In Hydrogenated Amorphous Silicon Devices," B. G. Yacobi, pp. 695–697, Appl. Phys. Lett. 44 (7), Apr. 1, 1984.

Primary Examiner—Daniel Robinson

(57) ABSTRACT

A swallowable data recorder medical device includes a capsule including a sensing module for sensing a biologic condition within a body. A recording module is provided including an atomic resolution storage device. The recording module is electrically coupled to the sensing module for recording data representative of the sensed biologic condition in the atomic resolution storage device. A power supply is coupled to the recording module.

21 Claims, 6 Drawing Sheets

U.S. PATENT DOCUMENTS

| | | | |
|---|---|---|---|
| 5,803,914 A * | 9/1998 | Ryals et al. | 600/407 |
| 5,925,030 A | 7/1999 | Gross et al. | |
| 5,984,875 A | 11/1999 | Brune | |
| 6,068,853 A | 5/2000 | Giannos et al. | |
| 6,132,372 A * | 10/2000 | Essen-Moller | 600/431 |
| 6,240,312 B1 | 5/2001 | Alfano et al. | |
| 6,352,502 B1 * | 3/2002 | Chaiken et al. | 600/473 |
| 6,402,692 B1 * | 6/2002 | Morford | 600/301 |
| 6,416,474 B1 | 7/2002 | Penner et al. | |
| 6,428,469 B1 | 8/2002 | Iddan et al. | |
| 6,510,380 B1 | 1/2003 | Curatolo et al. | |
| 6,561,978 B1 | 5/2003 | Conn et al. | |
| 6,584,348 B2 * | 6/2003 | Glukhovsky | 600/547 |
| 6,587,710 B1 * | 7/2003 | Wainer | 600/427 |
| 6,681,133 B2 * | 1/2004 | Chaiken et al. | 600/473 |

\* cited by examiner

SWALLOWABLE DATA RECORDER CAPSULE MEDICAL DEVICE

This application is a divisional of 09/710,161 filed Nov. 8, 2000 now U.S. Pat. No. 6,632,175.

CROSS REFERENCE TO RELATED APPLICATIONS

This patent application is related to Non-Provisional U.S. patent application Ser. No. 09/710,028, entitled "INTERNAL DRUG DISPENSER CAPSULE MEDICAL DEVICE," which is filed on even date herewith, is assigned to the same assignee as the present application, and is herein incorporated by reference.

THE FIELD OF THE INVENTION

The present invention relates to intrabody sensors, and in particular an ingestible data recorder capsule medical device which senses and records information within a body.

BACKGROUND OF THE INVENTION

Obtaining information about biologic conditions on the inside of the body poses at least two basic issues. First, one must place a sensing device in the body at the desired location. For example, to obtain data about biologic conditions on the large intestine or colon, one must insert a sensor at that location. Second, the data obtained must be transmitted from the internal location to a remote location outside of the human body for processing, storage and/or analysis.

In one example, a conventional endosoope inserted within a colon can obtain internal information about the colon, such as an image of any polyps in the colon, and then transmit that image to a remote location for real time viewing and/or storage. Unfortunately, use of an endoscope is quite invasive requiring insertion of a probe within the colon and simultaneous extension of communication lines from the probe to a location outside of the colon. Moreover, in addition to manual insertion, this method requires manually maintaining the position of the sensing device, e.g. probe, within the body. Accordingly, only locations within the body that are reachable by insertable probes can be monitored using this method.

In another example, an inert, ingestible medical capsule is known which is capable of sensing temperature within the digestive tract and then transmitting that temperature data to a receiver located remotely outside of the body. Since the capsule is inert, i.e. non-digestible, the capsule can be reused for subsequent procedures. Use of this medical capsule requires the patient to be located closely to the remote data receiver for an extended period of time to insure that the sensed data is properly transmitted to the remote receiver.

Perhaps more importantly, this conventional capsule is limited to sensing a single type of data, e.g. temperature. Moreover, the amount of data recorded remotely is limited by the size and strength of components located within the capsule, such as the size and amount of memory storage available within the capsule, the size and strength of transmitter in the conventional capsule, as well as by the associated wireless communication technique. Naturally, these constraints artificially limit the amount and types of biologic data that could otherwise be sensed and recorded throughout the digestive tract since the biologic information available is virtually limitless.

Accordingly, conventional intrabody sensors have several limitations. First, manual insertion of sensors limit the number and type of body locations that can be monitored and also require extensive remote (i.e. outside of the body) equipment support during the procedure. Second, more mobile sensors, such as ingestible capsules, require a remote receiver for receiving data transmitted from the capsule. This requirement forces the patient to remain relatively stationary for a protracted period of time during the procedure, or forces the patient to wear some form of remote receiver. Finally, the conventional capsule is limited in the amount and type of data sensed and recorded.

SUMMARY OF THE INVENTION

The present invention provides a swallowable data recorder medical device. The swallowable data recorder medical device includes a capsule enclosing a sensing module for sensing a biologic condition within a body. A recording module is provided including an atomic resolution storage device. The recording module is electrically coupled to the sensing module for recording data representative of the sensed biologic condition in the atomic resolution storage device. A power supply is coupled to the recording module.

DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

The present invention provides a swallowable data recorder capsule medical device which internally senses and internally records information about biologic conditions within the digestive tract of a body. The capsule is inert and therefore ingestible and passable through the digestive tract without being consumed. Accordingly, the swallowable sensor and recorder optimally is used in sensing and recording information about the digestive tract or about chemical conditions or conditions within the digestive tract that are indicative of conditions in other organs (e.g., skin). Preferably all of the biologic information sensed within the digestive tract is recorded immediately in an atomic resolution storage device or atomic resolution memory within the capsule while the capsule is in the digestive tract. The sensed data is conveniently retrievable from the atomic resolution storage device memory after the capsule is captured outside of the body.

The atomic resolution storage device memory used in the swallowable data recorder capsule medical device according to the present invention is subminiature in size, allowing it to be contained within a swallowable capsule, has low power requirements, and provides for non-volatile storage of large amounts of data, including video. The term "atomic resolution storage device" memory as used herein is defined as a non-volatile memory storage device capable of storing a large volume of data, such as megabytes to gigabytes of data points, within a relatively small storage area and requiring very low power consumption. The atomic resolution storage device includes a field emitter, a storage medium, and a micromover and associated circuitry for the reading and writing of data. Preferably, the atomic resolution storage device includes a plurality of spaced apart field emitters, wherein each field emitter is responsible for a number of storage areas on the storage medium.

Figure 1:
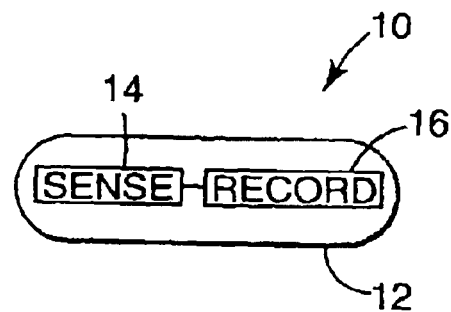
FIG. 1 is a schematic illustration of one exemplary embodiment of a swallowable data recorder capsule medical device, according to the present invention.

As shown generally in FIG. 1, a swallowable data recorder capsule medical device 10 of the present invention includes a capsule housing or capsule shell 12 containing sensing module 14 and recording module 16. Capsule 10 is readily ingestible within a digestive tract of a human body and is inert (i.e. non-digestible) so that capsule 10 passes through the digestive tract without being consumed. Sensing module 14 senses one or more predetermined biologic condition(s) within the human body such as temperature, pH, biological/chemical constituents, and/or visually recognizable landmarks internally within the human body, etc. Recording module 16 records, within capsule 10, a digital representation of the data sensed by sensing module 14. Accordingly, after ingestion, capsule 10 senses one or more predetermined biologic conditions within a digestive tract of the human body and then stores that biologic information "on-board" within capsule 10 as data in recording module 16. In one preferred embodiment, the stored data is retrieved after capsule 10 is captured outside of the human body.

Figure 2:
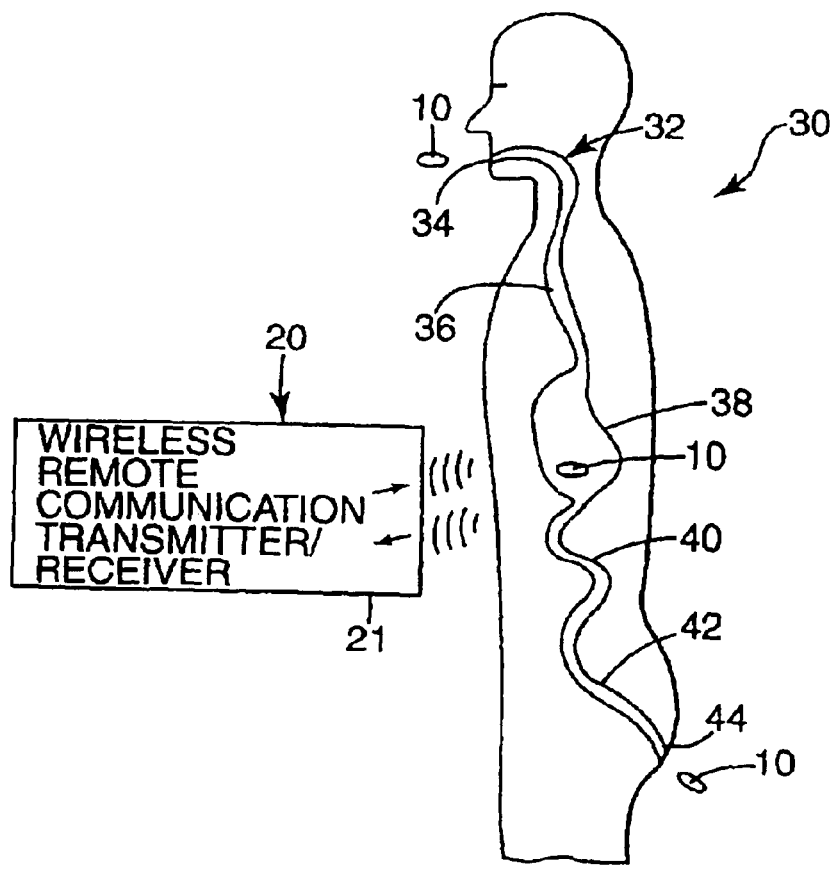
FIG. 2 is a sectional view of a digestive tract of a human body showing the travel path of a swallowable data recorder capsule medical device, according to an embodiment of the present invention.

FIG. 2 shows capsule 10 in association with human body 30 including digestive tract 32 having mouth 34, esophagus 36, stomach 33, small intestine 40, large intestine 42, and rectum 44. Once ingested within mouth 34, inert capsule 10 travels the full path of digestive tract 32 until capsule 10 is captured upon exiting at rectum 44. Each of the named locations within the human body represents examples of locations at which capsule 10 can sense and record data regarding biologic conditions. Of course, operation of capsule 10 is not limited to use in the named locations as capsule 10 can sense and record data anywhere within digestive tract 32. More importantly, recording module 16 has sufficient capacity to store data from multiple locations within digestive tract 34 and regarding several biologic parameters.

Capsule 10, particularly its shell 12, preferably is made of or coated with one or more of the following inert materials: Teflon (i.e., polytetrafluouroethylene); glass; ceramic; or other materials known to those skilled in the art. Other suitable materials will become apparent to those skilled in the art after reading the present application. Capsule 10 preferably has a size as large as the digestive tract will allow, such as five millimeters in diameter, and preferably has a generally rounded oblong shape, as shown in FIG. 1. However, other shapes and sizes can be used (e.g., a smaller capsule), provided that the shapes are readily passable through digestive tract 34 and can adequately house the required sensing and recording module 14,16.

Capsule 10 is capable of continuously sensing biologic conditions and continuously recording that sensed data within the capsule 10. Alternatively, each of the sensing and recording functions can be selectively controlled using remote wireless communication techniques for selective activation at a predetermined body location or at a predetermined point in time. Accordingly, as shown in FIG. 2, capsule 10 optionally comprises a larger system including wireless communication system 20 with transmitter/receiver 21 that operates (i.e., communicates) with a transmitter/receiver (not shown) incorporated in capsule 10. Finally, capsule 10 optionally continuously senses biologic conditions and then records data or only selectively records data (representative of those conditions) upon the sensed data reaching a predetermined value of one or more predetermined parameters (e.g., temperature, pH, etc.).

Figure 3:
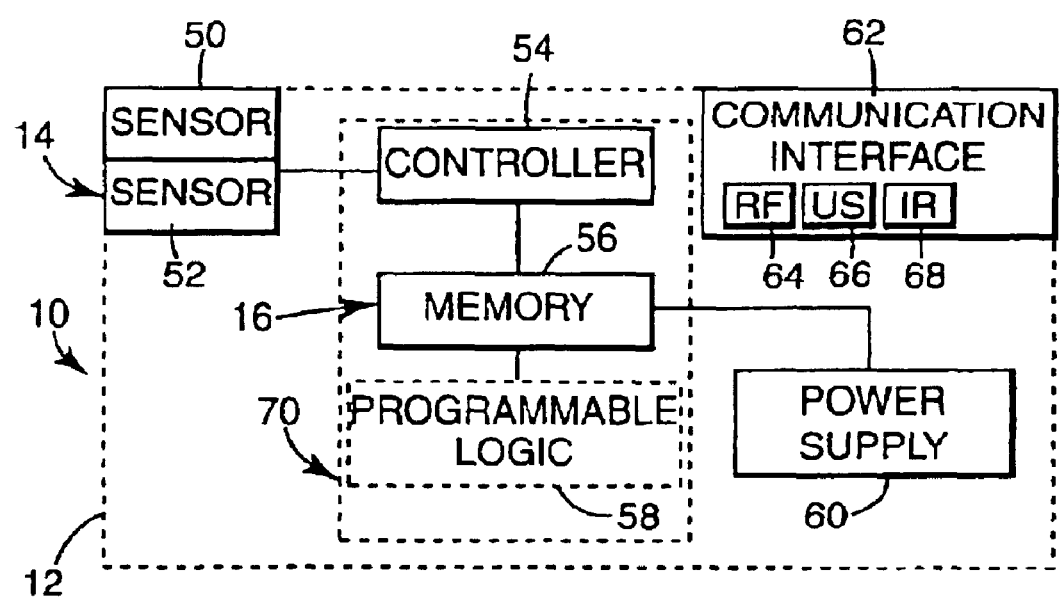
FIG. 3 is a block diagram of a swallowable data recorder capsule, according to an embodiment of the present invention.

FIG. 3 is a block diagram illustrating one exemplary embodiment of swallowable data recorder capsule 10, illustrating capsule 10 in greater detail. As shown in FIG. 3, recorder capsule 10 includes sensors 50, 52, controller 54, memory 56, optional programmable logic 58, power supply 60, and communication interface 62. Communications interface 62 may include one or more of the following types of communication modules: radiofrequency 64; ultrasonic 66; and/or infrared 68. Other suitable communication modules will become apparent to those skilled in the art after reading the present application. Finally, at least memory 56, and preferably also controller 54 and/or programmable logic 58 are embodied on a recording module 70, and preferably on a silicon-based module 70 in one or more semiconductor chips.

Sensors 50, 52 further define sensing module 14 of FIG. 1. Sensors 50, 52 define multiple sensors that are arranged about an outer surface of capsule 10 in a desired predetermined orientation to expose each sensor to a targeted bodily condition or landmark target within the human body. Each sensor can comprise a single type of sensor such as an image detector or a different type of sensor (e.g. chemical, electrical, temperature, etc.). For example, chemical detectors detect the presence of many substances, such as the concentration of glucose, which is relevant to treatment of diabetes patients.

Controller 54 regulates communication between sensors 50, 52 and memory 54, communication between memory 54 and any remote controllers outside of the human body, and communication with programmable logic component(s) 58. Finally, controller 54 operably controls communication interface 62 and preferably includes a central processing unit or one or more other devices capable of performing a sequence of logical operations. In one preferred embodiment, controller 54 is a microprocessor. In another embodiment, controller 54 includes one or more logic gates located within memory 56.

Memory or storage device 56 is preferably an ultra-high capacity storage device, and which is more preferably of a silicon-based construction. In one preferred embodiment, memory 56 is an atomic resolution storage device capable of storing a large volume of data, such as megabytes to gigabytes of data points, within a relatively small storage area. The atomic resolution storage device is a low power consumption storage device, requiring only about 0.1 watts or less to operate. In one preferred embodiment, ARS module 70 has a size of about 1 square millimeter, suitable to be carried within a swallowable medical capsule. In addition, ARS module can include its own modules that correspond to the functions of programmable logic 58 and/or controller 54. Finally, other subminiature memory devices, known to those skilled in the art, that have a high storage capacity with relatively low power consumption can be used in place of ARS module. However, these alternative devices may limit the volume and quality of data recorded since these devices will not be as powerful as ARS module 70 relative to the power consumption requirements and amount of memory storage.

One atomic resolution storage device suitable for use in the swallowable data recorder capsule medical device according to the present invention is disclosed in U.S. Pat. No. 5,557,596 to Gibson et al., issued Sep. 17, 1996, entitled "Ultra-High Density Storage Device." Other suitable ultra-high density storage devices suitable for use as memory 56 with the swallowable data recorder capsule medical device according to the present invention will become apparent to those skilled in the art after reading the present application. One exemplary embodiment of a suitable ultra-high density storage device (i.e., atomic resolution storage device) suitable for use as memory 56 with the swallowable data recorder capsule medical device according to the present invention is disclosed in further detail later in this application.

A suitable power supply 58 includes a lithium-ion battery, which is relatively non-toxic, as well as other power supplies suitable for in vivo environments.

Communication interface 62 includes a suitable transmission technology, preferable wireless (e.g. ultrasonic, radiofrequency, etc.), that readily permits communication to and from capsule 10 while capsule is in digestive tract 34 and remote transmitter/receiver 21 (FIG. 1) is located remotely outside of the body. However, infrared port 68 is preferably used for communicating with capsule 10 after capsule 10 is captured from the body to retrieve sensed data from memory 56. Likewise, infrared port 68 preferably is used for programming controller 54, memory 56, and/or logic component 58 prior to insertion of capsule 10 within the body to determine the manner in which sensors 50,52 will operate and communicate with memory 56 via controller 54.

In use, sensors 50,52 of capsule 10 sense biologic data within digestive tract 34 and the sensed data is passed through controller 54 for storage in memory 56. The sensed data is stored in memory 56 and retrieved via communication interface 62 after capture of capsule 10 upon exiting digestive tract 34. Finally, wireless communication system 20 optionally is used in addition to, or as an alternative to, controller 54 and memory 56 to facilitate and retrieving storing sensed data. The most significant aspect of capsule 10 is recording module 16 including memory 56, which permits internally recording within capsule 10 a profile of one or more biologic parameters throughout the entire digestive tract. This feature eliminates the need for transmission of data to a remote receiver as well as expands the type and amount of biologic data sensed and recorded.

FIGS. 4 through 7 disclose one exemplary embodiment of an atomic resolution storage device capable of storing megabytes to gigabytes of information in a small storage area. For a further discussion of an atomic resolution storage device, see U.S. Pat. No. 5,557,596, entitled, "Ultra-High Density Storage Device", by Gibson et al. and assigned to Hewlett-Packard Company, which is incorporated herein by reference.

Figure 4:
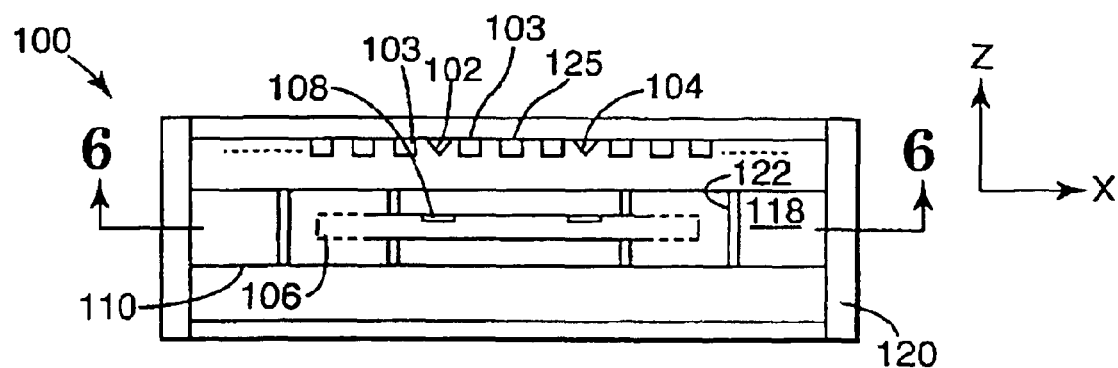
FIG. 4 is a side view illustrating one exemplary embodiment of a storage device used in a swallowable data recorder capsule medical device in accordance with the present invention.

FIG. 4 illustrates a side cross-sectional view of storage device 100. Storage device 100 is one exemplary embodiment of storage device recorder 54 including memory 56. Storage device 100 includes a number of field emitters, such as field emitters 102 and 104, storage medium 106 including a number of storage areas, such as storage area 108, and micromover 110. Micromover 110 scans storage medium 106 with respect to the field emitters or vice versa. In one preferred embodiment, each storage area is responsible for storing one bit of information.

In one embodiment, the field emitters are point emitters having relatively very sharp points. Each point emitter may have a radius of curvature in the range of approximately 1 nanometer to hundreds of nanometers. During operation, a pre-selected potential difference is applied between a field emitter and its corresponding gate, such as between field emitter 102 and gate 103 surrounding it. Due to the sharp point of the emitter, an electron beam current is extracted from the emitter towards the storage area. Depending on the distance between the emitters and the storage medium 106, the type of emitters, and the spot size (bit size) required, electron optics may be utilized to focus the electron beams. A voltage may also be applied to the storage medium 106 to either accelerate or decelerate the field-emitted electrons or to aid in focusing the field-emitted electrons.

In one embodiment, casing 120 maintains storage medium 106 in a partial vacuum, such as at least $10^{-5}$ torr. It is known in the art to fabricate such types of microfabricated field emitters in vacuum cavities using semiconductor processing techniques. See, for example, "Silicon Field Emission Transistors and Diodes," by Jones, published in IEEE Transactions on Components, Hybrids and Manufacturing Technology, 15, page 1051, 1992.

In the embodiment shown in FIG. 4, each field emitter has a corresponding storage area. In another embodiment, each field emitter is responsible for a number of storage areas. As micromover 110 scans storage medium 106 to different locations, each emitter is positioned above different storage areas. With micromover 110, an array of field emitters can scan over storage medium 106.

As will be described, the field emitters are responsible to read and write information on the storage areas by means of the electron beams they produce. Thus, field emitters suitable for use in storage device 100 are the type that can produce electron beams that are narrow enough to achieve the desired bit density on the storage medium, and can provide the power density of the beam current needed for reading from and writing to the medium. A variety of ways are known in the art that are suitable to make such field emitters. For example, one method is disclosed in "Physical Properties of Thin-Film Field Emission Cathodes With Molybdenum Cones," by Spindt et al, published in the Journal of Applied Physics, Vol. 47, No. 12, Dec. 1976. Another method is disclosed in "Fabrication and Characteristics of Si Field Emitter Arrays," by Betsui, published in Tech. Digest 4$^{th}$ Int. Vacuum Microelectronics Conf., Nagahama, Japan, page 26, 1991.

In one embodiment, there can be a two-dimensional array of emitters, such as 100 by 100 emitters, with an emitter pitch of 50 micrometers in both the X and the Y directions. Each emitter may access tens of thousands to hundreds of millions of storage areas. For example, the emitters scan over the storage areas with a periodicity of about 1 to 100 nanometers between any two storage areas. Also, all of the emitters may be addressed simultaneously or sequentially in a multiplexed manner. Such a parallel accessing scheme significantly reduces access time, and increases data rate of the storage device.

Figure 5:
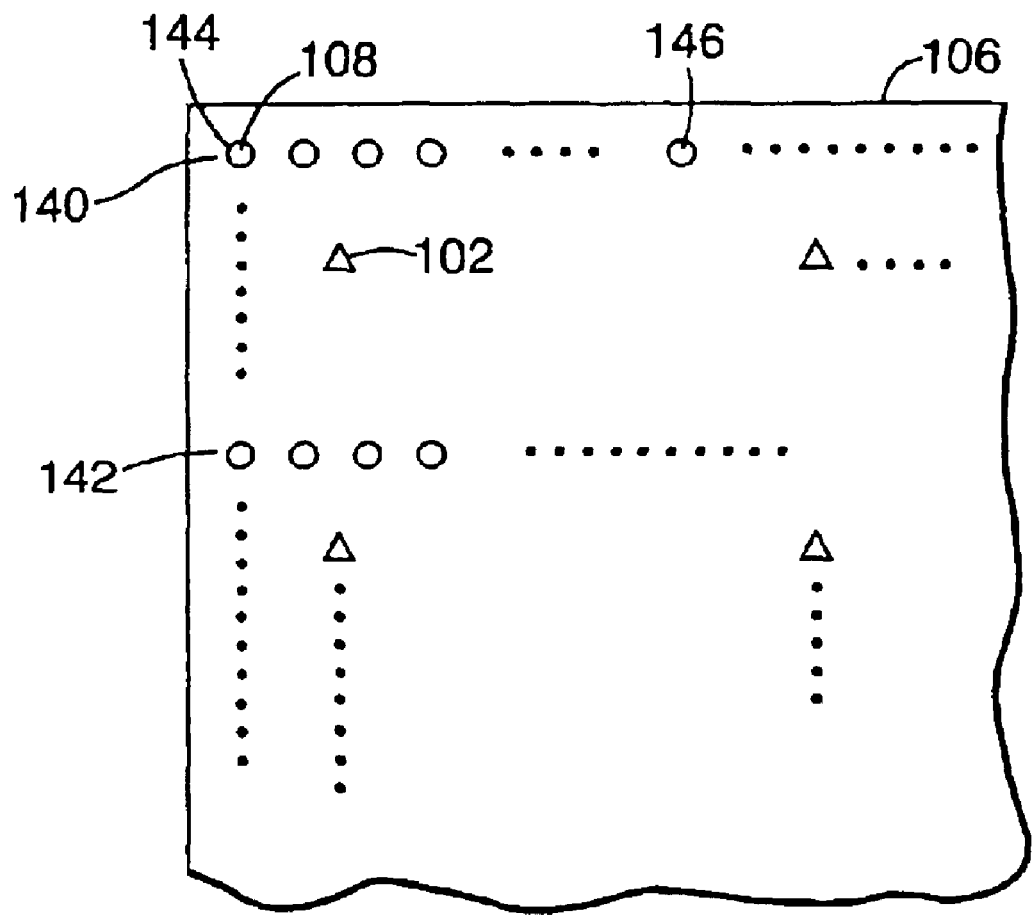
FIG. 5 is a simplified schematic diagram illustrating one exemplary embodiment of storing information within the storage device illustrated in FIG. 4.

FIG. 5 shows the top view of storage medium 100 having a two-dimensional array of storage areas and a two-dimensional array of emitters. Addressing the storage areas requires external circuits. One embodiment to reduce the number of external circuits is to separate the storage medium into rows, such as rows 140 and 142, where each row contains a number of storage areas. Each emitter is responsible for a number of rows. However, in this embodiment, each emitter is not responsible for the entire length of the rows. For example, emitter 102 is responsible for the storage areas within rows 140 through 142, and within columns 144 through 146. All rows of storage areas accessed by one emitter are connected to one external circuit. To address a storage area, one activates the emitter responsible for that storage area and moves that emitter by micromover 110 (shown in FIG. 4) to that storage area The external circuit connected to the rows of storage areas within which that storage area lies is activated.

Micromover 110 can also be made in a variety of ways, as long as it has sufficient range and resolution to position the field emitters over the storage areas. As a conceptual example, micromover 110 is fabricated by standard semiconductor microfabrication process to scan storage medium 106 in the X and Y directions with respect to casing 120.

Figure 6:
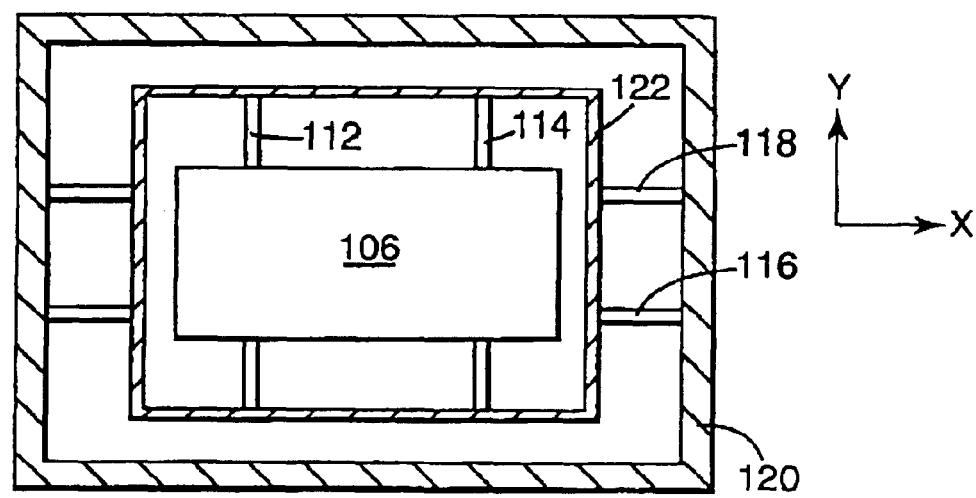
FIG. 6 is a top view illustrating one exemplary embodiment of a storage device used in a swallowable data recorder in accordance with the present invention taken along lines 6—6 of FIG. 4.

FIG. 6 shows the top view of the cross section 6—6 in FIG. 4, illustrating storage medium 106 held by two sets of thin-walled microfabricated beams. The faces of the first set of thin-walled beams are in the Y–Z plane, such as 112 and 114. Thin-walled beams 112 and 114 may be flexed in the X direction allowing storage medium 106 to move in the X direction with respect to casing 120. The faces of the second set of thin-walled beams are in the X–Z plane, such as 116 and 118. Thin-walled beams 116 and 118 allow storage medium 106 to move in the Y direction with respect to casing 120. Storage medium 106 is held by the first set of beams, which are connected to frame 122. Frame 122 is held by the second set of beams, which are connected to casing 120. The field emitters scan over storage medium 106, or storage medium 106 scans over the field emitters in the X–Y directions by electrostatic, electromagnetic, piezoelectric, or other means known in the art. In this example, micromover 110 moves storage medium 106 relative to the field emitters. A general discussion of such microfabricated micromover can be found, for example, in "Novel Polysilicon Comb Actuators for XY-Stages," published in the Proceeding of MicroElectro Mechanical Systems 1992, written by Jaecklin et al.; and in "Silicon Micromechanics: Sensors and Actuators on a Chip", by Howe et al., published in IEEE Spectrum, page 29, in July 1990.

In another embodiment, the electron beam currents are rastered over the surface of storage medium 106 by either electrostatically or electromagnetically deflecting them, such as by electrostatic deflectors or electrodes 125 (shown in FIG. 4) positioned adjacent to emitter 104. Many different approaches to deflect electron beams can be found in literature on Scanning Electron Microscopy and will not be further described in this specification.

In one method, writing is accomplished by temporarily increasing the power density of the electron beam current to modify the surface state of the storage area. Reading is accomplished by observing the effect of the storage area on the electron beams, or the effect of the electron beams on the storage area. For example, a storage area that has been modified can represent a bit 1, and a storage area that has not been modified can represent a bit 0, and vice versa. In fact, the storage area can be modified to different degrees to represent more than two bits. Some modifications may be permanent, and some modifications may be reversible. The permanently modified storage medium is suitable for write-once-read-many memory (WORM).

In one embodiment, the basic idea is to alter the structure of the storage area in such a way as to vary its secondary electron emission coefficient (SEEC), its back-scattered electron coefficient (BEC), or the collection efficiency for secondary or back-scattered electrons emanating from the storage area. The SEEC is defined as the number of secondary electrons generated from the medium for each electron incident onto the surface of the medium. The BEC is defined as the fraction of the incident electrons that are scattered back from the medium. The collection efficiency for secondary/back-scattered electrons is the fraction of the secondary/back-scattered electrons that is collected by an electron collector, typically registered in the form of a current.

Reading is typically accomplished by collecting the secondary and/or back-scattered electrons when an electron beam with a lower power density is applied to storage medium 106. During reading, the power density of the electron beam should be kept low enough so that no further writing occurs.

One embodiment of storage medium 106 includes a material whose structural state can be changed from crystalline to amorphous by electron beams. The amorphous state has a different SEEC and BEC than the crystalline state, which leads to a different number of secondary and back-scattered electrons emitted from the storage area. By measuring the number of secondary and back-scattered electrons, one can determine the stage of the storage area. To change from the amorphous to crystalline state, one increases the beam power density and then slowly decreases it. This heats up the amorphous and then slowly cools it so that the area has time to anneal into its crystalline state. To change from crystalline to amorphous state, one increases the beam power density to a high level and then rapidly decreases the beam power. To read from the storage medium, a lower-energy beam strikes the storage area. An example of such type of material is germanium telluride (GeTe) and ternary alloys based on GeTe. Similar methods to modify states using laser beams as the heating source have been described in "Laser-induced Crystallization of Amorphous GeTe: A Time-Resolved Study," by Huber and Marinero, published in Physics Review B 36, page 1595, in 1987, and will not be further described here.

There are many preferred ways to induce a state change in storage medium 106. For example, a change in the topography of the medium, such as a hole or bump, will modify the SEEC and BEC of the storage medium. This modification occurs because the coefficients typically depend on the incident angle of the electron beam onto the storage area. Changes in material properties, band structure, and crystallography may also affect the coefficients. Also, the BEC depends on an atomic number, Z. Thus, one preferred storage medium has a layer of low Z material on top of a layer of high Z material or vice versa, with writing accomplished through ablating some of the top layer by an electron beam.

Figure 7:
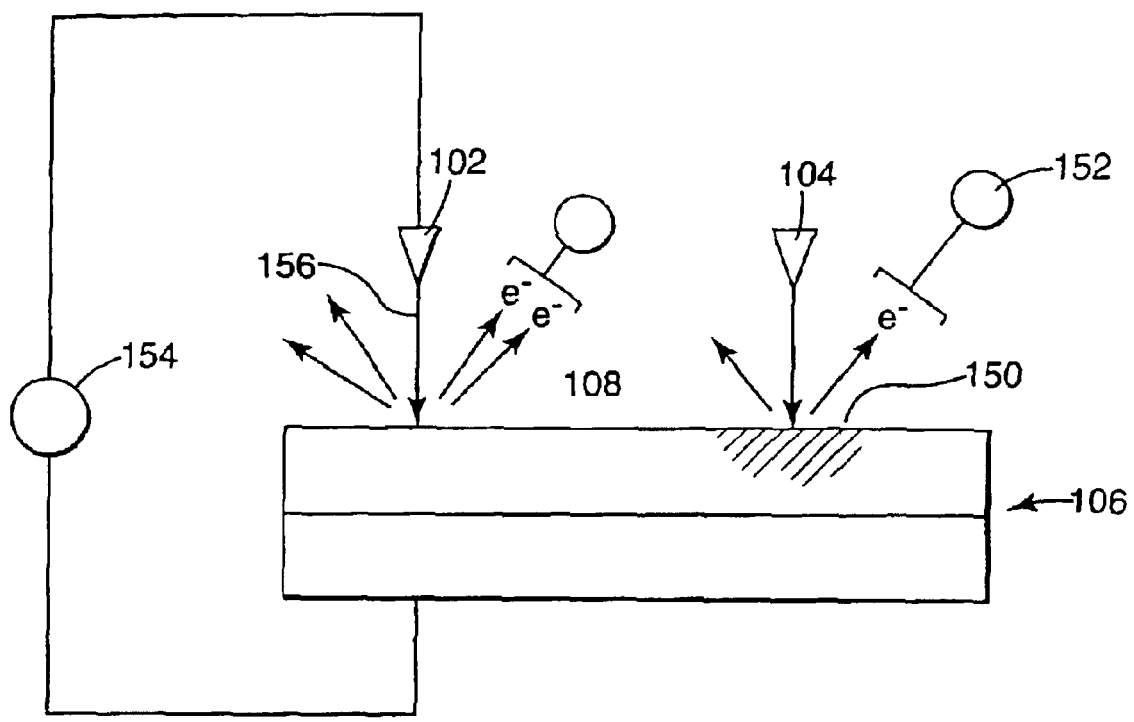
FIG. 7 is a diagram illustrating one exemplary embodiment of field emitters reading from storage areas of the storage device of FIG. 4.

FIG. 7 shows schematically the field emitters reading from storage medium 106. The state of storage area 150 has been altered, while the state of storage area 108 has not been altered. When electrons bombard a storage area, both secondary electrons and back-scattered electrons will be collected by the electron collectors, such as electron collector 152. An area that has been modified will produce a different number of secondary electrons and back-scattered electrons, as compared to an area that has not been modified. The difference may be more or may be less depending on the type of material and the type of modification. By monitoring the magnitude of the signal current collected by electron collectors 152, one can identify the state of and, in turn, the bit stored in, the storage area.

Figure 8:
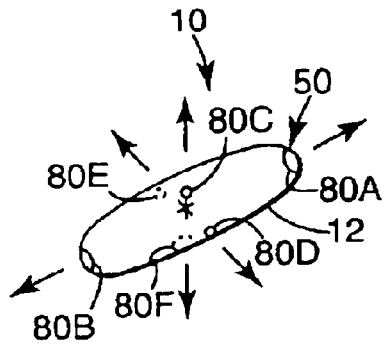
FIG. 8 is a perspective view of a swallowable data recorder capsule incorporating an image detector array, according to an embodiment of the present invention.

Field emitters may be noisy with the magnitude of the electron beam current varying with respect to time. Moreover, the gap distance between the tips of the emitters and the surface of the storage medium may vary. If the information stored were based on tunneling current, then the gap distance may be extremely crucial. However, the application presently disclosed depends on field emitters, and not directly on the emitted electron beam current, but rather on the effect of the beam. At least two ways may be used to alleviate the problem of the emitters being noisy. One way is to connect constant current source 154 to field emitter 102. This source will control the power density of electron beam current beam 156. Although this method would not help storage techniques using the magnitude of the field emitted current as the signal, this method reduces the field emitter noise significantly. Another way to alleviate the field-emitter noise is to separately measure the emitted electron beam current and use it to normalize the signal current. As the electron beam current varies, the signal current varies correspondingly. On the other hand, the normalized signal current remains the same to indicate the state of the storage area FIG. 8 is a perspective view of capsule 10 in which sensor array 80 further defines sensors 50, 52 and includes sensors 80A, 80B, 80C, 80D, 80E, and 80F. Each sensor 80A–80F can represent a single type of sensor such as an image detector or a different type of sensor (e.g. chemical, electrical, temperature,etc.). Alternatively, multiple sensors (e.g. sensors 80C, 80D) can represent a single type of sensor. Sensor array 80 is arranged to sense data along the six cardinal directions using the classical major and minor axes of the generally elliptical-shaped capsule 10. However, sensor array 80 can include more or less than six sensors and need not be oriented along the six cardinal directions but along other multi-directional orientations as desired. Accordingly, sensor array 80 illustrates that multiple sensors are arranged about the capsule surface in a desired predetermined orientation that is expected to expose each sensor, or the full array, to a targeted bodily condition or landmark within the human body.

Figure 9:
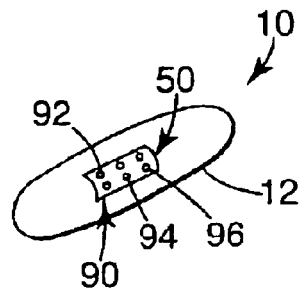
FIG. 9 is a perspective view of a sensor array of a swallowable data recorder capsule, according to an embodiment of the present invention.
Figure 10:
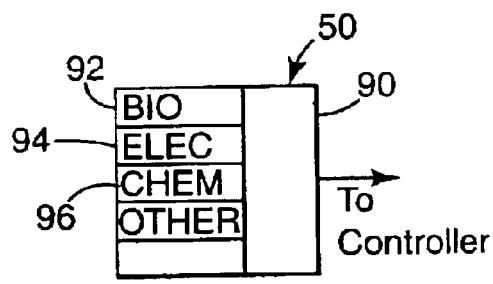
FIG. 10 is a schematic illustration of the swallowable data recorder capsule of FIG. 9.

FIG. 9 is perspective view of capsule 10, in which sensor module 90 further defines sensor 50 and includes sensors 92, 94, 96. Each sensor 92, 94, 96 represents the same type of sensor. Alternatively, as shown in FIG. 10, sensor array 90 may include sensors 92, 94, 96 which each comprise a different type of sensor. For example, sensor 92 comprises a biologic condition sensor (e.g. pH), sensor 94 comprises an electrical sensor (e.g. temperature), and sensor 96 comprises a chemical sensor (e.g. sodium and/or potassium).

Sensing module 90 preferably is a silicon-based module, which includes various cavities filled with the desired type of sensing substance and/or circuitry to form each sensor 92, 94, 96. For example, sensor 90 preferably is constructed from a silicon surface bearing a chemically sensitized film for each sensor 92, 94, 96, wherein the film reacts upon the presence of a particular biologic constituent, producing an electrical response in the silicon surface that is recorded in memory as sensed data Suitable sensor modules 90 are known in the art, such as are available from Agilent Technologies (e.g., an Agilent 2100 bioanalyzer).

For example, using these techniques sensor 92 can be selected to sense absolute values of pH, or sense pH only below a certain value, e.g. 5. Sensor 92 also could be selected to sense any pH value to provide continuously variable data on pH.

Alternatively, sensor 92 could sense the presence of any expected digestive tract constituent such as bile fluids, or any unexpected digestive tract constituent such as blood, or cancer cells. For example, one of the sensors 92, 94, 96 could be chemically sensitive to cancer cells. Upon a sensor detecting a cancer cell constituent, the data is recorded. After retrieving the data outside of the body, the location in digestive tract 34 is determined based on the character of the sensed data and is used to target future diagnostic and/or therapeutic techniques to that location. Alternatively, radiographic or wireless communication techniques can be used to identify the location of capsule 10 upon the sensed data triggering a transmission signal to a remote receive.

This type of sensor array 90 conveniently permits a large number of the same type or different type of sensors to be placed on small electrically communicable module. This arrangement is preferred where many different types of tests must be performed. For example, in investigative research, comprehensive information can be gathered about many biologic conditions with one pass of capsule 10, rather than checking for a single biologic condition with each pass of capsule 10.

Figure 11:
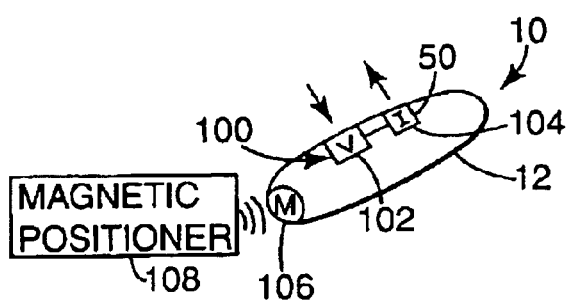
FIG. 11 is a schematic illustration of a swallowable data recorder capsule incorporating a video recorder module, according to an embodiment of the present invention.

FIG. 11 is a perspective view of a data recorder capsule of the present invention including a video and illumination capsule in which sensors 50, 52 further include a video module 102 and illumination module 104 (e.g., a light emitting diode), in which video images are received by video module 102 and illumination module 104 acts to illuminate the subject under investigation. While not shown in FIG. 7, video module 102 and illumination module 104 are connected to the remainder of the system shown in FIG. 3. Subminiature video receiving and illumination devices known to those skilled in the art can be used. The high capacity storage device memory 56 allows for large amounts of video data to be stored in capsule 10.

As shown in FIG. 11, this embodiment also optionally further includes magnetic member 106 within capsule 10 and remote magnetic positioner 108 (for placement outside of the body) to assist in positioning capsule 10 within digestive tract 34 to obtain a desired image using video module 102. To orient capsule 10 within digestive tract 34, magnetic positioner 108 is manipulated outside the body to direct capsule 10 into a desired orientation. Magnetic member 106 and magnetic positioner 108 can be incorporated into any of the other embodiments of capsule 10 described herein.

A swallowable medical capsule of the present invention has many advantageous features. Foremost, after sensing biologic conditions within a digestive tract, the capsule immediately records that sensed biologic data in memory within the capsule while still in the digestive tract. The sensed data is retrieved later after the capsule is captured upon exit from the digestive trace The ultra large storage capacity of the memory within the capsule along with the use of silicon-based surface sensing modules (or other types of sensors, e.g., imaging) permits large volumes of many different types of biologic conditions to be sensed and recorded internally for later study. In addition, this internal recording feature alleviates the prior art need to immediately transmit sensed data from the capsule inside the digestive tract to a receiver remotely located away from the capsule outside of the body. Accordingly, a patient no longer must remain in close proximity to a receiving device during the time period that the capsule is within the human body. Rather, the patient can move freely, making more likely that such a capsule will be used. Nevertheless, for ultimate flexibility, the internal recording ability also can be used at the same time as known wireless data transmission techniques to both immediately transmit sensed data to a remote location and to record the data internally within the capsule. Finally, unlike the use of endoscopes, use of the capsule is essentially non-invasive, which will likely cause more patients to agree to a diagnostic sensing procedure using the capsule. The capsule may also be implanted at a desired location within a body for long periods of time, sense and record data, and be removed at a later date for data retrieval and analysis.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electro-mechanical, electrical, and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A swallowable data recorder medical device comprising:
   a capsule including:
   a sensing module for sensing a biologic condition within a body, the sensing module including a video receiver, wherein sensing the biologic condition includes the video receiver receiving video of the biologic condition;
   a recording module including an atomic resolution storage device, the recording module electrically coupled to the sensing module for recording data representative of the sensed biological condition, in the atomic resolution storage device; and
   a power supply coupled to the recording module.

2. The device of claim 1, wherein the sensing module further includes an illumination source.

3. The device of claim 1, wherein the sensing module provides an output signal representative of the sensed biological condition, and the recording module includes a controller for receiving the output signal from the sensing module.

4. The device of claim 3, wherein the controller performs one or more logical operations using the output signal, and selectively provides output data to the atomic resolution storage device based upon the logical operations.

5. The device of claim 1, wherein the recording module includes programmable logic.

6. The device of claim 5, wherein the programmable logic is located on the atomic resolution storage device.

7. The device of claim 1, wherein the atomic resolution storage device further comprises:
   a field emitter fabricated by semiconductor microfabrication techniques capable of generating an electron beam current; and
   a storage medium in proximity to the field emitter and having a storage area in one of a plurality of states to represent the information stored in the storage area via the field emitter, representative of the sensed biological condition.

8. The device of claim 7, wherein an effect is generated when the electron beam current bombards the storage area, wherein a magnitude of the effect depends upon the state of the storage area, and wherein the information stored in the storage area is read by measuring the magnitude of the effect.

9. The device of claim 7, further comprising:
   a plurality of storage areas on the storage medium, with each storage area being in one of the plurality of states to represent the information stored in the storage area; and
   a microfabricated mover in the storage device to position different storage areas to be bombarded by the electron beam current.

10. The device of claim 9, further comprising:
    a plurality of field emitters, with each emitter being fabricated by semiconductor microfabrication techniques capable of generating an electron beam current, the plurality of field emitters being spaced apart, with each emitter being responsible for a number of storage areas on the storage medium;
    wherein the plurality of the field emitters work in parallel to increase the data rate of the storage device.

11. The device of claim 1, wherein the sensing module includes at least one of a chemical detector and an electrical detector.

12. The device of claim 1, wherein an outer surface of the capsule is made of an inert material.

13. The device of claim 1, further comprising a magnetic member, wherein the magnetic member permits manipulation of the capsule from a location outside the body.

14. An ingestible data recorder medical device comprising:
    a capsule including:
    a sensing module for-sensing,a biologic condition within a body, wherein sensing the biologic condition includes receiving video of the biologic condition;
    a recording module including:
    a controller for performing one or more logical operations using the sensed biological condition; and
    an atomic resolution storage device, wherein the recording module is electrically coupled to the sensing module for selectively recording data representative of the sensed biological condition to the storage device based upon the logical operations.

15. The device of claim 14, wherein the recording module includes programmable logic.

16. The device of claim 14, wherein the capsule further includes a magnetic member to facilitate manipulation of the capsule from a location outside the body.

17. An ingestible data recorder medical device comprising:
   a capsule including:
   means for sensing a biological condition within a body, the means for sensing a biological condition includes a means for sensing images of the biologic condition;
   means for storing the biological condition including an atomic resolution storage device; and
   means for recording the biological condition to the means for storing the biological condition.

18. The device of claim 17, wherein the means for recording the biological condition is configured to selectively record the biological condition to the means for storing the biological condition based upon predetermined parameters.

19. The device of claim 17, wherein the means for sensing a biological condition includes a means for sensing at least one of a chemical condition or an electrical condition.

20. The device of claim 17, further comprising:
   means for positioning the capsule to obtain desired images from within the body.

21. The device of claim 17, the means for recording comprises a video receiver.

* * * * *